United States Patent [19]

Alig et al.

[11] 4,036,874
[45] * July 19, 1977

[54] D-HOMOPREGNANES

[75] Inventors: Leo Alig, Liestal; Andor Fürst, Basel; Marcel Müller, Frenkendorf, all of Switzerland

[73] Assignee: Hoffmann-La Roche Inc., Nutley, N.J.

[*] Notice: The portion of the term of this patent subsequent to Feb. 17, 1993, has been disclaimed.

[21] Appl. No.: 639,939

[22] Filed: Dec. 11, 1975

Related U.S. Application Data

[63] Continuation-in-part of Ser. No. 345,149, March 26, 1973, abandoned.

[30] Foreign Application Priority Data

Mar. 29, 1972 Switzerland .................. 4666/72

[51] Int. Cl.$^2$ ............................... C07J 63/00
[52] U.S. Cl. ..................... 260/488 B; 195/51 S; 195/51 A; 260/340.9; 260/348 A; 260/408; 260/410; 260/468 R; 260/469; 260/474; 260/476 C; 260/485 F; 260/485 G; 260/486 H; 260/486 R; 260/586 E; 424/234; 424/305; 424/308; 424/311; 424/312; 424/313; 424/314; 424/331
[58] Field of Search .................. 260/488 B, 586 E

[56] References Cited

U.S. PATENT DOCUMENTS 2,860,158 11/1958 Clinton ......................... 260/488 B
3,939,193 2/1976 Alig et al. ..................... 260/488 B Primary Examiner—Vivian Garner
Attorney, Agent, or Firm—Samuel L. Welt; George M. Gould; Raymond R. Wittekind

[57] ABSTRACT

D-homosteroids of the formula

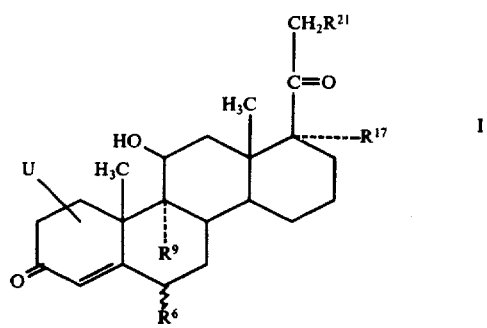

wherein $R^6$ is hydrogen, fluorine, chlorine or methyl; $R^9$ is hydrogen, fluorine, chlorine or bromine; $R^{17}$ and $R^{21}$ each independently are hydroxy or acyloxy, and U represents optional olefinic unsaturation are endocrine agents having anti-inflammatory properties.

16 Claims, No Drawings

D-HOMOPREGNANES

This application is a continuation-in-part of copending U.S. Patent Application Ser. No. 345,149 filed Mar. 26, 1973, now abandoned.

BRIEF DESCRIPTION OF THE INVENTION

The present invention relates to novel steroids of the pregnane series. More specifically, the compounds of the present invention are D-homosteroids represented by the general formula

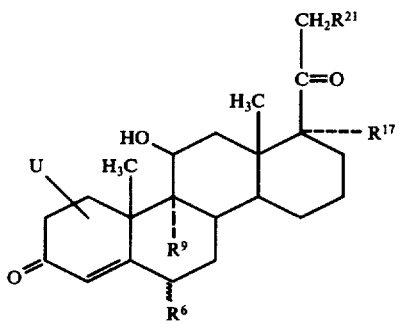

wherein $R^6$ is hydrogen, fluorine, chlorine or methyl; $R^9$ is hydrogen, fluorine, chlorine or bromine; $R^{17}$ and $R^{21}$ each independently are hydroxy or acyloxy, and U represents optional olefinic unsaturation.

The aforementioned acyloxy groups are preferably derived from alkane mono- or di- carboxylic acids, e.g., formic acid, acetic acid, pivalic acid, propionic acid, butyric acid, caproic acid, oenanthic acid, palmitic acid, stearic acid, succinic acid, malonic acid, and so forth; alkene mono-or di- carboxylic acids, e.g., oleic acid, fumaric acid, maleic acid, and so forth; cycloalkanoic acids, e.g., cyclopentylacetic acid, cyclohexylacetic acid, cyclohexylpropionic acid, and so forth; arylalkanoic acids, e.g., phenylacetic acid, phenylpropionic acid, naphthylacetic acid, and so forth; and aroci acids, e.g., benzoic acid, salicyclic acid, naphthoic acid, and so forth. Especially preferred acyloxy groups are those derived from acids containing up to and including 12 carbon atoms.

A preferred group of compounds of formula I are those in which $R^6$ and $R^9$ are hydrogen or fluorine and $R^{17}$ and $R^{21}$ are hydroxy or alkanoyloxy of up to 6 carbon atoms. Especially preferred are those compounds wherein U represents olefinic unsaturation between the 1- and 2- positions of the steroid nucleus. Of those compounds which are substituted in the 6-position by other than hydrogen, the 6α isomers are preferred.

In the formulae presented herein, the various substituents are joined to the cyclic nucleus by one of three notions: a solid line (—), indicating a substituent which is in the β-orientation (above the plane of the paper), a dotted line (--), indicating a substituent which is in the α-orientation (below the plane of the paper), or a wavy line (∽), indicating a substituent which may either be in the α- or β-orientatin. The position of the methyl groups in the 10- and 13-positions have been arbitrarily indicated as the β-orientation which is consistent with the absolute stereochemistry of the products described in the examples. It is to be understood, however, that in the formulae presented both in the specification and in the appended claims, there is intended to be represented both of the enantiomeric series, as well as mixtures thereof, such as racemic mixtures.

The compounds of formula I may be prepared in a variety of fashions from simpler compounds, utilizing synthetic methods well known to those skilled in the steroid art. Most of these methods involve the introduction and/or transformation of the various substituent groups present on the compounds of formula I to arrive at a specifically desired compound.

The following methods are briefly summarized, although precedent is found for each of these methods in the prior art for steroids having a 5-membered D-ring:

Steroids of formula I may be prepared by hydroxylating the 11-position of a D-homosteroid of the general formula

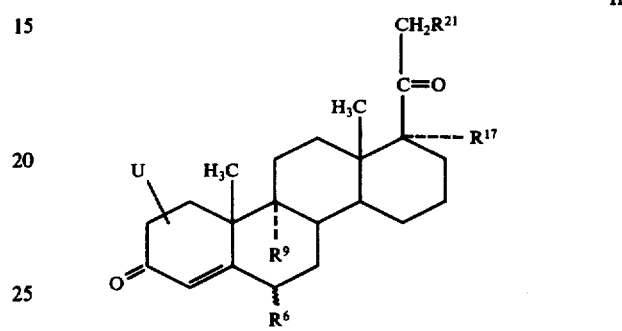

wherein $R^6$, $R^9$, $R^{17}$, $R^{21}$ and U are as above. This hydroxylation can be performed using methods which are known per se for the microbiological introduction of an 11-hydroxy group into steroids. For this reaction, there may be used microorganisms of the taxanomic unit Fungi and Schizomycetes, especially of the subunit Ascomycetes, Phycomycetes, Basidiomycetes and Actinomycetales. Mutants produced by chemical means (e.g., by treatment with nitrite) or by phsical means (e.g., by irradiation), as well as cell-free enzyme preparations obtained from the microorganisms can also be used. Suitable microorganisms for the 11β-hydroxylation are particularly those of the genus Curvularia, e.g., C. lunata NRRL 2380 and NRRL 2178, Absidia, e.g., A. coreula IFO 4435, Colletotrichum, e.g., C. pisi ATCC 125j20, Pellicolaria, e.g., P. filamentosa IFO 6675, streptomyces, e.g., S. fradie ATCC 10745, Cunninghamella, e.g., C. bainieri ATCC 9244, C. verticellata ATCC 8983, C. elegans ATCC 9245 and C. echinulata ATCC 8984, and Pycnosporium, e.g., sp. ATCC 12231.

A second method for the preparation of compounds of formula I involves replacement of a 21-halogen atom in a D-homosteroid of the formula

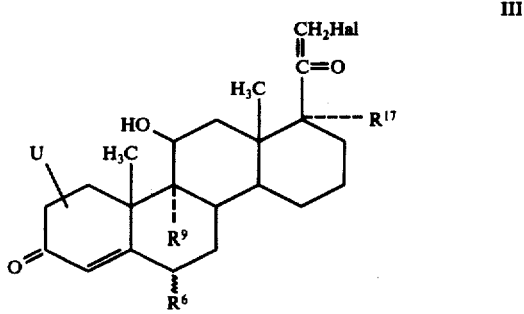

wherein $R^6$, $R^9$, $R^{17}$ and U are as above and Hal is chlorine, bromine or iodine. In such a procedure, the desired compound of formula III is warmed with an appropriate alkali metal acylate in the presence of the acid corresponding to the acylate, for example, with potassium acetate inglacial actic acid.

Compounds of formula I which are saturated at the 1,2-positions of the steroid nucleus may be converted to their 1,2-dehydro derivatives by methods known per se. For example, these conversions can be effected by microbiological means or by means of dehydrogenating agents such as iodine pentoxide, periodic acid, selenium dioxide, 2,3-dichloro-5,6-dicyanobenzoquinone, chloranil or lead tetraacetate. Suitable microorganisms for the 1,2-dehydrogenation are, for instance, Schizomycetes, particularly those of the genus Arthrobacter, e.g. A. simplex ATCC 6946, Bacillus, e.g., B. lentus ATCC 13805 and B. sphaericus ATCC 7055, Pseudomonas, e.g., P. aeruginosa IFO 3505, Flavobacterium, e.g., F. flavescens IFO 3085, Lactobacillus, e.g., L. brevis IFO 3345 and Nocardia, e.g., N. opaca ATCC 4276.

In still another procedure, compounds of formula I may be prepared from compounds of the formula

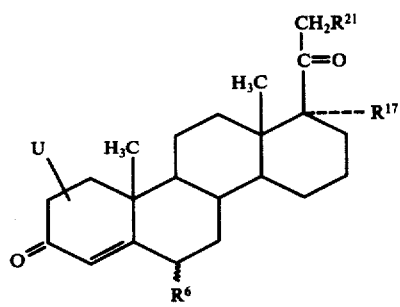

IV wherein $R^6$, $R^{17}$, $R^{21}$ and U are as above. In such a process the compound of formula IV is dissolved in a suitable solvent, preferably an ether such as tetrahydrofuran or dioxane; or a chlorinated hydrocarbon such as methylene chloride or chloroform; or a ketone such as acetone, and reacted with hypochlorous or hypobromous acid. the hydrochlorous or hypobromous acid is conveniently formed in situ in the reaction mixture; for example, from N-bromo or N-chloramides or -imides such as N-chlorosuccinimide or N-bromoacetamide and a strong acid, preferably perchloric acid.

In yet another procedure, compounds of formula I may be prepared from compounds of the formula

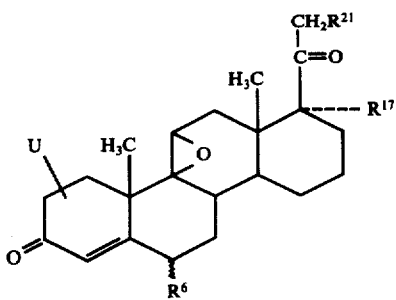

V wherein $R^6$, $R^{17}$ and $R^{21}$ and U are as above. By means of this procedure, theD-homosteroids of formula V are dissolved in an inert solvent and the solution treated with the appropriate hydrogen halid. This embodiment is the preferred method for the manufacture of 9-fluoro- D-homosteroids of formula I.

Acyloxy groups present on the 17- and 21-positions of the steroid nucleus in compounds of formula I may be saponified to afford the corresponding hydroxy groups. Methods for saponification are known per se; for example, using aqueous-methanolic potassium carbonate solution or potassium hydroxide solution.

In yet another procedure, 6β-fluoro-, chloro- or -methyl-D-homosteriods of formula I can be isomerized to the corresponding 6α- compounds by treatment with an acid, preferably a mineral acid such as hydrochloric acid in a solvent such as dioxane or glacial acetic acid. This procedure is most useful for the isomerization of 6-fluoro and 6-chloro compounds.

In still another procedure, fluorine or chlorine may be introduced into the 6-position of the steroid nucleus by treating a compound of one of the formulae

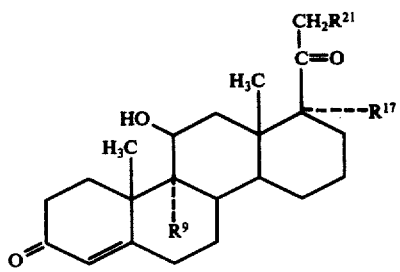

VI

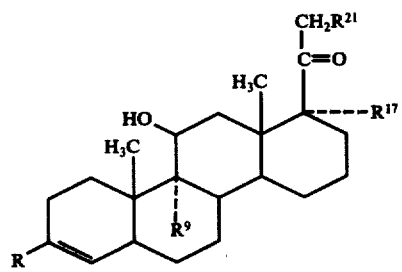

VIa wherein $R^9$, $R^{17}$ and $R^{21}$ are as above, and R is lower acyloxy or lower alkoxy. Such a procedure can be effected by treatment of one of the aforesaid compounds with a chlorination agent such as elemental chlorine, an N-chlorimide (for example, N-chlorosuccinimide) or an N-chloroamide (for example, N-chloroacetamide). Fluorination may be effected by treatment of one of the aforesaid compounds with perchloryl fluoride. Mixtures of 6α- and 6β- isomers can be separated by usual physical means such as crystallization or chromatography.

The 17a- and 21- hydroxy groups in a D-homosteroid of the formula

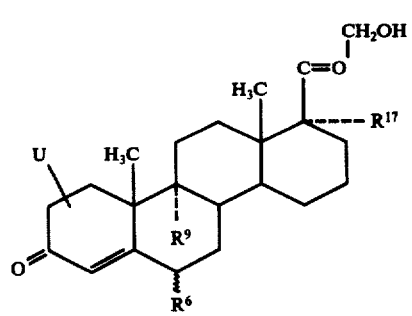

VII wherein $R^6$, $R^9$ and U are as above, may be acylated according to methods known per se. Such methods involve treatment with an acylating agent such as an acyl chloride, for example, acetyl chloride; or an acid anhydride, for example, acetic anhydride, in the presence of an acid binding agent such as a tertiary amine, for example, pyridine or triethylamine. The acylation of a 17a- hydroxy group is preferably carried out in the presence of an acid catalyst such as p-toluenesulphonic acid.

Compounds of formula I may also be prepared by dehydration of a D-homosteriod of the formula

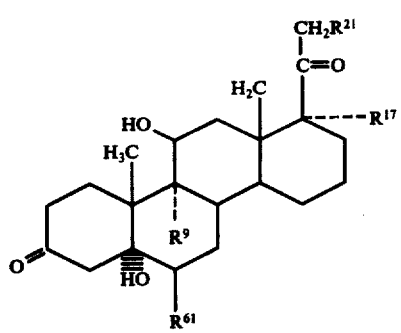

VIII wherein $R^9$, $R^{17}$ and $R^{21}$ are as above and $R^{61}$ is fluorine or chlorine. Such a dehydration is effectively performed by treatment with a strong acid for example, a mineral acid such as hydrochloric acid or an organic sulphonic acid such as p-toluenesulphonic acid.

Compounds of formula I may also be prepared by reduction of the 11-keto group of a compound of the formula

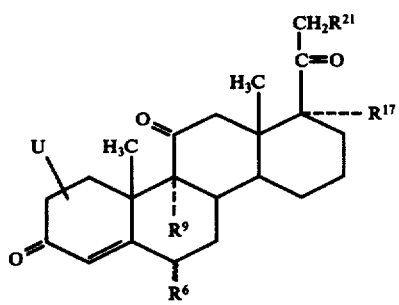

IX wherein $R^6$, $R^9$, $R^{17}$, $R^{21}$ and U are as above. In carrying out such a procedure, the keto groups in the 3- and 20-positions of the D-homosteroid of formula IX are first protected, for example, by ketalization. Where $R^{17}$ and $R^{21}$ both represent hydroxy groups, a 20-keto group can also be protected by formation of the 17a, 20; 20, 21-bismethylenedioxy derivative. The reduction of the 11-keto group of protected D-homosteriods can be carried out using a complex metal hydride such as lithium aluminum hydride, sodium borohydride or diisobutyl aluminum hydride.

The introduction of the oxygen functions into the 17a- and 20-positions of the steroid can be accomplished by oxidizing the 17(20)-double bond of a D-homosteroid of the formula

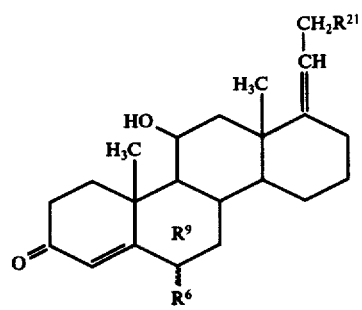

X wherein $R^6$, $R^9$ and $R^{21}$ are as above. The oxidation process can be carried out, for example, by using oxidizing agents such as a tertiary amine N-oxide peroxide in tertiary butanol/pyridine in the presence of catalytic amounts of osmium tetroxide. Example of tertiary amine N-oxide peroxides are N-methylmorpholine N-oxide peroxide and triethylamine N-oxide peroxide. On the other hand, one can oxidize to a 17a,20-glycol using an oxidizing agent such as osmium tetroxide or permaganate and then further oxidize the 17,20-glycol to the desired hydroxy keton using an oxidizing agent such as chronic acid.

One further method for the preparation of compounds of formula I involves the dehydrohalogenation of a D-homosteroid of the formula

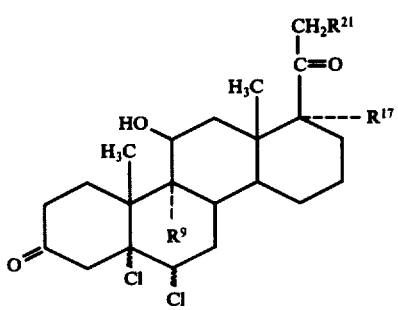

XI wherein $R^9$, $R^{17}$ and $R^{21}$ are as above. Such a dehydration may be accomplished by use of a base, preferably an organic base such as a tertiary amine, for example, pyridine or triethylamine.

Additional method for effecting the various conversions and transformations to prepare compounds of formula I will be readily apparent to one skilled in the art.

The starting materials used in the aforementioned processes, insofar as they may be unknown or are described hereinafter, may be prepared in analogy to known methods or to methods described below. Generally, D-homosteroids are conveniently prepared by a Tiffeneau ring enlargement of a 17-aminomethyl-17-hydroxy steroid to afford a D-homosteroid having a 17a-keto group. The pregnane side chain may be added by a variety of methods, for example, conversion of the 17a-ketone to its ethylidene derivative by means of a Wittig reaction and further oxidation of the 17(20) double bond as described above.

The D-homosteroids of the present invention possess endocrine activity, especially anti-inflammatory activity. For example, in the felt-pellet test in the rat, a 40% inhibition of granuloma formation was achieved with the following dosages: 2.7 mg.kg of D-homo- 11β,17aα,21-trihydroxy-pregn-4-en-3,20-dione; 0.9 mg/kg of D-homo-11β,17aα,21-trihydroxypregna-1,4-dien-3,20-dione; 0.35 mg/kg of D-homo11β,17aα,21-trihydroxy-9αfluoro-pregn-4-en-3,20-dione and 0.05 mg/kg of D-homo-11β,17aα,21-trihydroxy-9αfluoro-pregna-1,4-dien-3,20-dione.

The D-homosteroids represented by formula I can e used as medicaments; for example, in the form of pharmaceutical preparation which contain compounds of formula I in association with a compatible pharmaceutical carrier. This carrier may be an inert organic or inorganic carrier material suitable for enteral, percutaneous or parenteral adminstration; for example, water gelatin, gum arabic, lactose, starch, magnesium stearate, talc, vegetable oils, polyalkylene glycols, petroleum jelly and so forth. Pharmaceutical preparations can be made up in solid form (for example, as tablets, dragees, suppositories or capsules), in semi-solid form (for example, as ointments), or in liquid form (for example, as solutions, suspensions or emulsions). If necessary, the pharmaceutical preparations may be sterilized and/or may contain adjuvants such as preservatives, stabilizers, wetting agents, emulsifiers, salts for varying the osmotic pressure or buffers. They can also contain other therapeutically valuable substances.

The present invention will be further understood and appreciated by reference to the following examples:

EXAMPLE 1

3.81 g of D-homo-11β,17a α-dihydroxy-pregn-4en-3,20-dione in 20ml of methanol are mixed with 4.7 ml of 10% methanolic calcium chloride solution and 2.3 g of ignited calcium oxide. Then a solution of 3.5 g of iodine and 2.2 g of calcium chloride in 22 ml of methanol is slowly added dropwise and the mixture is stirred for about a further 10 minutes. The mixture is poured onto ice-water and extracted with methylene chloride. The methylene chloride extracts are washed with water, dried and evaporated. The crude iodide obtained is dissolved in 56 ml of acetone, the solution mixed with 0.56 ml of water, 0.56 ml of glacial acetic acid and 5.6 g of potassium acetate and boiled under reflux for 18 hours. The solution is concentrated and worked up with water/methylene chloride. Chromatography of the crude product on silicagel gives D-homo-21-acetoxy-11β, 17aα-dihydroxy-pregn-4-en-3,20-dione of melting point 212°-213° C; $[\alpha]_D = +145$ °(c = 0.104 in dioxane).

The starting material can be prepared as follows:

3,11β-Diacetoxy-androsta-3,5-dien-17-one is reacted in methylene chloride with ethylene glycol in the presence of orthoformic acid ester and p-toluenesulphonic acid at room temperature to give 3,11β-acetoxy-17,17-ethylenedioxy-androsta-3,5-diene of melting point 183°-186° C; $[\alpha]_D = -112°(c=0.104$ in dioxane); $\epsilon_{235} = 19,700$.

The foregoing 17-ketal is reduced in tetrahydrofuran/methanol with sodium borohydride to give 11β-acetoxy-17,17-ethylenedioxy-3β-hydroxyandrost-5-ene of melting point 125°-126° C;$[\alpha]_D = -66°$ (c = 0.102 in dioxane).

Cleavage of the thus-obtained ketal in aqueous acetone with p-toluenesulphonic acid gives 11β-acetoxy-3β-hydroxy-androst-5-en-17-one of melting point 193°-195° C; $[\alpha]_D = -4°$ (c = 0.102 in dioxane).

The resulting 17-ketosteroid is reacted with dimethylsulphoxonium methylide in dimethylformamide to give 21-nor-11β-acetoxy-17,20ε-epoxy-3β-hydroxypregn-5-ene of melting point 155°-156° C; $[\alpha]_D = -52°$ (c = 0.103 in dioxane).

The foregoing epoxide is reacted in alcohol and concentrated ammonia in an autoclave to give 11β-acetoxy-17ε-aminomethyl-3β,17ε-dihydroxyandrost-5-ene. By reaction with sodium nitrite in glacial acetic acid and water there is obtained D-homo-11β-acetoxy-3β-hydroxy-androst-5-en-17a-one of melting point 230°-232° C;$[\alpha]_D = -121°$(c = 0.103 in dioxane).

Saponification of the thus-obtained 11β-acetate in boiling methanolic potassium hydroxide gives D-homo-3β,11β-dihydroxy-androst-5-en-17a-one of melting point 234°-236° C;$[\alpha]_D = -143°$ (c = 0.107 in dioxane).

The resulting 3,11-diol is reacted in dimethyl sulphoxide with sodium hydride and triphenylethylphosphonium bromide to give D-homo-3β,11β-dihydroxy-pregna-5,17a(20)-diene of melting point 172°-173° C;$[\alpha]_D = -137°$ (c = 0.104 in dioxane).

Subsequent oxidation according to the Oppenauer method gives D-homo-11 β-hydroxy-pregna-4,17a(20)-dien-3-one of melting point 160°-161° C; $[\alpha]_3 = +96°$ (c = 0.102 in dioxane); $\epsilon_{243} = 15,000$.

Oxidation of the 4,17a(20)-diene thus obtained with osmium tetroxide and N-methylmorpholine oxide/hydrogen peroxide gives D-homo-11β, 17aα-dihydroxy-pregn-4-en-3,20-dione of melting point 213°-215° C; $[\alpha]_3 = +104°$ (c = 0.102 in dioxane); $\epsilon_{242} = 16,250$.

EXAMPLE 2

In an analogous manner to that described in Example 1, from D-homo-11β, 17aα-dihydroxy-pregna-1,4-dien-3,20-dione there is obtained D-homo-21-acetoxy-11β, 17aα-dihydroxy-pregna-1,4-dien-3,20-dione of melting point 220°-222° C; $[\alpha]_D = +108°$ (c = 0.105 in dioxane); $\epsilon_{242} = 14,500$.

The starting material can be prepared by the microbiological dehydrogenation of D-homo-11β-17a α-dihydroxy-pregn-4-en-3,20-dione with Arthrobacter simplex to give D-homo-11β,17aα-dihydroxy-pregna-1,4-dien-3,20-dione of melting point 208°-212° C; $[\alpha]_D = +47°$ (c = 0.107 in dioxane); $\epsilon_{242} = 13,900$.

EXAMPLE 3

500 mg of D-homocortisol are stirred in 2 ml of pyridine and 2 ml of acetic acid anhydride for 24 hours at room temperature. The mixture is poured onto ice-cold dilute hydrochloric acid and extracted with methylene chloride. The extracts are washed with water, dried and evaporated. There is obtained pure D-homocortisol acetate which is identical with the product obtained according to Example 1.

EXAMPLE 4

1.25 g of D-homo-21-acetoxy-17aα-hydroxy-pregna-4,9(11)-dien-3,20-dione are dissolved in 53 ml of dioxane, mixed with 10.5 ml of water, 865 mg of N-bromoacetamide, 5.5 ml of 10% perchloric acid and stirred for 15 minutes at room temperature. Then 4.5 g of sodium sulphite and 90 ml of water are added. After stirring for a short time, the mixture is extracted with methylene chloride, the extracts are washed with water, dried over sodium sulphate and evaporated. There is obtained D-homo-21-acetoxy-11β, 17a α-dihydroxy-9 α-bromo-pregn-4-en-3,20-dione which is almost pure according to thin-layer chromatography.

The starting material can be prepared as follows:

D-Homohydrocortisone acetate is dehydrated in dimethylformamide with methanesulphonyl chloride in the presence of pyridine at an elevated temperature. There is obtained D-homo-21-acetoxy-17a α-hydroxy-pregna-4,9(11)-dien-3,20-dione of melting point 238°-240° C; $[\alpha]_D = +71°$ (c = 0.104 in dioxane); $\epsilon_{239} = 16,750$.

EXAMPLE 5

In an analogous manner to that described in Example 4, from D-homo-21-acetoxy-17a α-hydroxy-pregna-1,4,9(11)-trien-3,20-dione[melting point 188°-190° C; $[\alpha]_D = -1°$ (c = 0.084 in dioxane); $\epsilon_{238} = 16,700$] there is obtained D-homo-21-acetoxy-11β,17aα-dihydroxy-9α-bromo-pregna-1,4-dien-3,20-dione.

The starting material is prepared from D-homoprednisolone-21-acetate in an analogous manner to that described in the second paragraph of Example 4.

EXAMPLE 6

905 mg of D-homo-21-acetoxy-9,11β-epoxy-17aα-hydroxy-pregn-4-en-3,20-dione are stirred in 20 ml of a solution of 1.25 parts of hydrogen fluoride in 1 part of urea for 20 minutes at room temperature. The mixture is poured onto a mixture of 70 ml of concentrated ammonia and 200 g of ice and extracted with methylene chloride. The extracts are washed with sodium chloride solution, dried and evaporated. Chromatography on silicagel gives D-homo-21-acetoxy-11 β,17aα-dihydroxy-9α-fluoro-pregn-4-en-3,20-dione of melting point 242°-244° C; $[\alpha]_D = +137°$ (c = 0.102 in dioxane); $\epsilon_{239} = 16,220$.

As byproduce, D-homocortisone acetate, was also isolated.

The starting material can be prepared as follows:

D-Homo-21-acetoxy-9α-bromo-11 β, 17aα-dihydroxy-pregn-4-en-3,20-dione is boiled under reflux in absolute alcohol in the presence of anhydrous potassium acetate for 24 hours. There is obtained D-homo-21-acetoxy-9,11β-epoxy-17aα-hydroxy-pregn-4-en-3,20-dione of melting point 226°-228° C; $[\alpha]_D = +51°$ (c = 0.103 in dioxane); $\epsilon_{241} = 14,100$.

EXAMPLE 7

In an analogous manner to that described in Example 6, from D-homo-21-acetoxy-9,11β-epoxy-17aα-hydroxy-pregna-1,4-dien-3,20-dione [melting point 225°-226° C; $[\alpha]_D = +63°$(c = 0.103 in dioxane); $\epsilon_{248} = 16,900$ (prepared from D-homo-21-acetoxy-9α-bromo-11β,17a α-dihydroxy-pregna-1,4-dien-3,20-dione] there is obtained D-homo-21-acetoxy-9α-fluoro-11β,17a α-dihydroxy-pregna-1,4-dien-3,20-dione of melting point 240°-250° C; $[\alpha]_D = +109°$(c = 0.106 in dioxane); $\epsilon_{239} = 15,200$.

EXAMPLE 8

418 mg of D-homo-21-acetoxy-11β,17a α-dihydroxy-pregn-4-en-3,20-dione and 250 mg of selenium dioxide are stirred under reflux in 20 ml of tertbutanol and 0.2 ml of glacial acetic acid under argon for 20 hours. The mixture is filtered and evaporated. The oil obtained is dissolved in ethyl acetate and washed successively with sodium bicarbonate solution, water, ice-cold ammonium sulphide solution, dilute ammonia, water, dilute hydrochloric acid and water. The ethyl acetate solution is dried over sodium sulphate and evaporated in a vacuum. Chromatography on silicagel gives D-homo-21-acetoxy-11β,17aα dihydroxy-pregna-1,4-dien-3,20-dione of melting point 220°-222° C; $[\alpha]_D = +108°$ (c = 0.105 in dioxane); $\epsilon_{242} = 14,500$.

EXAMPLE 9

A suspension of 955 mg of D-homocortisol acetate in 16 ml of absolute methanol is flushed with argon. Then 250 mg of potassium carbonate in 3.5 ml of water are added dropwise and the mixture is stirred for 0.75 hour at room temperature. The mixture is then poured onto sodium chloride solution and extracted with methylene chloride. The extracts are washed, dried and evaporated. There is obtained pure D-homocortisol of melting point 245°-246° C; $[\alpha]_D = +142°$(c = 0.102 in dioxane); $\epsilon_{242} = 15,850$.

In a similar manner there are obtained:
from D-homoprednisolone-21-acetate
D-homoprednisolone of melting point 250° C (decomposition);
$[\alpha]_D = +105°$ (c = 0.101 in dioxane); $\epsilon_{242} = 14,400$;
from D-homo-9α-fluoro-cortisol-21-acetate
D-homo-9α-fluoro-cortisol of melting point
239°-241° C; $[\alpha]_D = +131°$ (c = 0.102 in dioxane); $\epsilon_{239} = 16,820$; and
from
D-homo-9 α-fluoro-prednisolone-21-acetate
D-homo-9 α-fluoro-prednisolone of melting point
241 °246° C (decomposition); $[\alpha]_D = +101°$ (c = 0.097
on dioxane); $\epsilon_{238} = 14,540$
from
6α-fluoro-D-homocortisol-21-acetate
6α-fluoro-D-homocortisol of melting point 233°-235° C;
$[\alpha]_D + 110°$ C (c = 0.103 in dioxane) $\epsilon_{236} = 13.400$
from
6α-fluoro-D-homoprednisolone-21-acetate
D-homo-9 α-fluoro-prednisolone-21-acetate
6α-fluoro-D-homoprednisolone of melting point 261°-264° C;
$[\alpha]_D + 93°$ (c = 0.106 in dioxane) $\epsilon_{241} = 15.200$.

EXAMPLE 10

500 ml of a sterile nutrient containing 5% starch syrup, 0.5% corn steep liquor, 0.2% sodium nitrate, 0.1% potassium dihydrogenphosphate, 0.05% potassium chloride, 0.05% magnesium sulfate, 0.002% ferrous sulfate is inoculated with Curvularia lunata NRRL 2380 from a two weeks old agar slant culture. The culture is grown for five days at 30° C with shaking. The so obtained culture serves to inoculate 15 liters of a sterile medium containing 5% starch syrup, 0.25% corn steep liquor, 0.1% sodium nitrate, 0.05% potassium dihydrogen phosphate, 0.025% potassium chloride, 0.025% magnesium sulfate, 0.001% ferrous sulfate. The culture is grown for 72 hours at 29° C with stirring (220 r.p.m.) and aeration (15 liters/min.). 900 ml of the so-obtained culture are transferred to a fermenter containing 14,1 liters of the nutrient medium described before. This culture is grown for 24 hours at 29° C with stirring and aeration. Thereafter, a solution of 3.0 g of 21-acetoxy-17aα-hydroxy-D-homo-pregn-4-ene-3,20-dione in 150 ml of dimethylformamide is filtered sterile and added. The culture is then incubated for another 40 hours, filtered and the filtrate and the mycelium is extracted with methyl isobutyl ketone. The extracts are combined and concentrated under reduced pressure. The residue is chromatographed on silicagel and the crude product recrystallized from acetone-hexane to yield D-homocortisol-21-acetate.

EXAMPLE 11

A nutrient medium consisting of 0.15% corn steep, 0.5% peptone and 0.5% glucose in distilled water, pH 7.3, is inoculated with Arthrobacter simplex ATCC 6946. The culture is grown for 24 hours at 28° C and then a solution of 25 mg of D-homocortisol in 1 ml of 80% aqueous ethanol is added. After an incubation time of 48–72 hours, the mycelia of the substrate are separated, washed with water and the washings and the substrate extracted with methylene chloride. Working up of the extract yields D-homo-11$\beta$,17a$\alpha$,21-trihydroxypregna-1,4-dien-3,20-dione(D-homoprednisolone).

EXAMPLE 12

690 mg of 6$\beta$-fluoro-D-homocortisol-21-acetate in 30 ml of acetic acid are mixed at room temperature with 0.3 ml of a 20 percent solution of hydrogen bromide in acetic acid. After 30 minutes, 1.5 ml of pyridine are added. The mixture is evapoarted and the residue is taken up in methylene chloride and washed with diluted sodium carbonate solution and water. The organic phase is dried over sodium sulfate and evaporated. Chromatography of the residue on silicagel using methylene chloride 5 percent acetone gives pure 6$\alpha$-fluoro-D-homocortisol-21-acetate of melting point 137°–139° C $[\alpha]_D + 110°$ C (c = 0.094 in dioxane), $\epsilon_{236} = 14.200$.

EXAMPLE 13

600 mg of D-homocortisol-21-acetate are dissolved in 6 ml of orthoethyl formate and 6 ml of absolute ethanol with heating. The solution is cooled to room temperature and a solution of 6 mg of p-toluene sulfonic acid in 6 ml of absolute ethanol is added. The mixture is left to stand at room temperature for 8 minutes. After one drop of pyridine is added the mixture is poured into water and extracted with methylene chloride. The organic phase is dried and evaporated and yields 700 mg of 21-acetoxy-3-ethoxy-11$\beta$,17a$\alpha$-dihydroxy-D-homo-pregna-3,5-diene-20-one, which is dissolved in 25 ml of dimethylformamide and 2.5 ml of water. Gaseous perchloryl fluoride is introduced at 0° C during 15 minutes. The reaction mixture is poured on ice water and extracted with methylene chloride. The organic phase is washed with water, dried and evaporated. There is obtained a mixture of 6$\alpha$-fluoro-D-homocortisol-21-acetate and its 6$\beta$-isomer in a ratio of about 1 : 5.

EXAMPLE 14

3.9 g of D-homo-21-acetoxy-11$\beta$-hydroxypregna-4,17a (20)-dien-3-one are dissolved in 95 ml of t-butanol. 7 ml of pyridine and subsequently, 20 mg of osmium tetroxide and 23 ml of 1,5 N N-methylmorpholine oxide/hydrogen peroxide solution in t-butanol are added. After 24 hours, a further 23 ml of N-methylmorpholine oxide/hydrogen peroxide are added. The reaction mixture is stirred for 24 hours, poured into water and thoroughly extracted with methylene chloride. The organic layers are washed with water, dried and evaporated. The crude oily product is chromatographed on silicagel and gives 1.3 g of D-homocortisol-21-acetate, which is identical with the product of Example 1.

EXAMPLE 15

In analogy to Example 6, there is obtained from D-homo-21 -acetoxy-9,11$\beta$-epoxy-6$\alpha$-fluoro-17a$\alpha$-hydroxypregna-1,4-diene-3,20-dione (prepared from D-homo-21-acetoxy-9$\alpha$-bromo-6$\alpha$-fluoro-11$\beta$,17a$\alpha$-dihydroxypregna-1,4-diene-3,20-dione) the compound D-homo-21-acetoxy-6$\alpha$,9$\alpha$-difluoro-11$\beta$, 17a$\alpha$-dihydroxypregna-1,4-diene-3,20-dione, melting point 240°–241° C $[\alpha]_D{}^{25} + 92°$ (c = 0.094 in dioxane), $\epsilon_{238} = 16,100$.

EXAMPLE 16

A mixture of 1.0 g of 5$\alpha$,6$\alpha$-dichloro-21-acetoxy-11$\beta$-17a$\alpha$-dihydroxy-D-homo-pregnane-3,20-dione, 1.0 g of anhydrous sodium acetate and 40 ml of 95 per cent ethanol is heated to reflux for 30 minutes. The reaction mixture is then poured into 250 ml of ice water and extracted with methylene chloride. The extract is washed with water, dried and evaporated. The residue is recrystallized from acetonehexane and yields pure 21-acetoxy-6$\beta$-chloro-11$\beta$,17a$\alpha$-dihydroxy-D-homo-pregn-4-ene-3,20-dione. The starting material can be prepared as follows: 21-acetoxy-11$\beta$-17a$\alpha$-dihydroxy-D-homopregn-4-ene-3,20-dione is reacted with ethylene glycol and p-toluene sulfonic acid in benzene to yield the 3-monoketal. The ketal is dissolved in chloroform and the solution treated with 1.05 equivalents chlorine at 0° C. The reaction mixture is allowed to warm to room temperature where upon nitrogen is bubbled through the solution. After washing and drying, the solution is evaporated on the residue left to stand with acetone 2 N for 5 hours at room temperature. Usual work-up gives the desired compound.

EXAMPLE 17

A mixture of 2.5 g of 21-acetoxy-6$\beta$-chloro-5$\alpha$,11$\beta$, 17a$\alpha$-trihydroxy-D-homo-pregna-3,20-dione, 250 ml of glacial acetic acid and 10 ml of conc. hydrochloric acid is left to stand for 17 hours at 5° C, then poured on ice water and extracted with methylene chloride. The extract is washed with sodium hydrogen carbonate solution and water until neutral, dried and evaporated under reduced pressure. The residue gives after recrystallization from acetone/hexane pure 21-acetoxy-6$\alpha$-chloro-11$\beta$,17a$\alpha$-dihydroxy-D-homo-pregn-4-ene-3,20-dione.

The starting material can be prepared as follows: 3,3-ethylenedioxy-21-acetoxy-11$\beta$,17a$\alpha$-dihydroxy-D-homopregn-5-ene-3,20-dione is oxidized with m-chloroperbenzoic acid to yield a mixture of the 5$\alpha$,6$\alpha$- and 5$\beta$,6$\beta$-epoxides. The 5$\alpha$,6$\alpha$-epoxide is isolated by chromatography and reacted with boron trichloride in ether to yield 3,3-ethylenedioxy-21-acetoxy-6$\beta$-chloro-5$\alpha$,11$\beta$,17a$\alpha$-trihydroxy-D-homopregnan-20-one which in turn is reacted with a little hydrochloric acid in acetone to give 21-acetoxy-6$\beta$-chloro-5$\alpha$,11$\beta$,17a$\alpha$-trihydroxy-D-homo-5$\alpha$-pregnane-3,20-dione.

EXAMPLE 18

3,5 g of 21-acetoxy-17a$\alpha$-hydroxy-D-homo-pregn-4-ene-3,11,20-trione is suspended in 50 ml of methanol and 2 ml of water. Nitrogen is blown through the suspension to remove oxygen. Thereafter, 2.7 g of semicarbazide hydrochloride and 1.5 g of sodium hydrogenacarbonate are added. The reaction mixture is heated to reflux for 3 ½ hours and subsequently kept ot 45° C for 20 hours. 80 ml of water are slowly added and the mixture is cooled to 0° C. The crystalline semicarbazone is sucked off and dried at 70° under reduced pressure. The semicarbazone is dissolved in 300 ml of tetrahydrofuran and reacted with a solution of 6.0 of sodiumborohydride in 100 ml of water. The reaction mixture is stirred at room temperature for 2 hours, cooled to 5° C, cautiously adjusted to pH 5.5 by the addition of acidic acid and concentrated. Water is then added and the mixture is filtered. The precipitate is dissolved in 500 ml of 2.5 N hydrochloric acid under nitrogen atmosphere. To this solution, a solution of 5 g of sodium nitrate in 50 ml of water is added within 10 minutes at 0°–5° C. After stirring for 30 minutes, a solution of 30 g of urea in 50 ml of water is added within 5 minutes. The resulting solution in neutralized with 20% sodium hydroxide solution at a temperature not exceeding 15° C and extracted with chloroform several times. The extract is evaporated to dryness and the residue after the addition of 50 ml of acetic anhydride and 50 ml of pyridine left to stand at room temperature for 2 hours. Usual work-up affords 14 g of crude product which after chromatography on silicagel yields pure 21-acetoxy-11β,17aα-dihyroxy-D-homo-pregn-4-ene-3-20-dione of melting point 212°–213° C.

EXAMPLE 19

In analogy to the process of Example 1 there is obtained from 6α-fluoro-11β,17aα-dihydroxy-D-homo-pregn-4-ene-3,20-dione the compound 21-acetoxy-6α-fluoro-11β,17aα-dihydroxy-D-homo-pregna-1,4-diene-3,20-dione, m.p. 229°–232° C $[\alpha]_D$ + 101 (c = 0.099 in dioxane) and 21-acetoxy-6α-fluoro-11β,17aα-dihydroxy-pregn-4-ene-3,20-dione, m.p. 137°–139° C $[\alpha]_D$ + 110° (c = 0.094 in dioxane) The preparation of the starting material: 11β,17aα-dihydroxy-D-homo-pregn-4-ene-3,20-dione is reacted with equal amounts of absolute ethanol and ethyl orthoformate in the presence of catalytic amounts of an acid for 10–15 minutes at room temperature to yield 3-ethoxy-11β, 17aα-dihydroxy-D-homo-pregna-3,5-dien-20-one. The enol ether is reacted with perchloryl fluoride in dimethylformamide/water to yield a mixture of 6α-fluoro-11β,17aα-dihydroxy-D-homo-pregna-4-ene-3,20-dione, m.p. 178°–180° C, $[\alpha]_D$ + 70° (c = 0.104 in dioxane) $E_{238}$ = 13.500 and its 6β-isomer, m.p. 196°–198°. The 6β-isomer can be isomerized to form the 6α-isomer by treatment with HBr in acetic acid.

We claim:

1. A compound of the formula

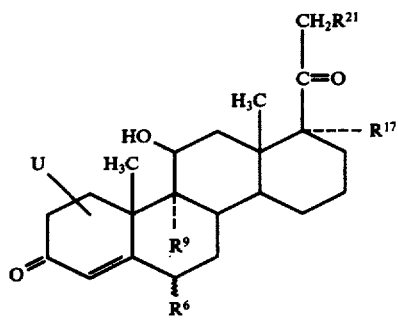

wherein $R^6$ is hydrogen, fluorine, chlorine or methyl and $R^9$ is hydrogen, fluorine, chlorine, or bromine with the provisos that $R^6$ and $R^9$ simultaneously are not hydrogen and $R^6$ is a group other than methyl when $R^6$ is hydrogen when U is hydrogen attached to each of the 1- and 2-positions of the steroid nucleus; $R^{17}$ and $R^{21}$ each independently are hydroxy or alkanoyloxy of up to 6 carbon atoms, and U is hydrogen attached to each of the 1- and 2-positions of the steroid nucleus or an additional single bond between the 1- and 2-positions of the steroid nucleus.

2. A compound according to claim 1 wherein $R^6$ represents 6αfluorine, chlorine or methyl.

3. A compound according to claim 1 which is D-homo-21-acetoxy-11β,17aα-dihydroxy-9α-bromo-pregn-4-en-3,20-dione.

4. A compound according to claim 1 which is D-homo-21-acetoxy-11β,17aα-dihydroxy-9α-bromo-pregna-1,4-dien-3,20-dione.

5. A compound according to claim 1 wherein $R^6$ and $R^9$ are hydrogen or fluroine with the proviso that $R^6$ and $R^9$ simultaneously are not hydrogen when U is hydrogen attached to each of the 1- and 2-positions of the steriod nucleus; and $R^{17}$ and $R^{21}$ are hydroxy or alkanoyloxy of up to 6 carbon atoms.

6. A compound according to claim 5 which is D-homo-21-acetoxy-11 β,17α-dihydroxy-9α-fluoro-pregn-4-en-3,20-dione.

7. A compound according to claim 5 which is D-homo-9α-fluorohydrocortisone.

8. A compound according to claim 5 which is 6α-fluoro-D-homocortisol.

9. A compound according to claim 5 which is 6α,9α-difluoro-D-homocoritsol.

10. A compound according to claim 5 wherein U is an additional single bond between the 1- and 2- positions of the steroid nucleus.

11. A compound according to claim 10 which is D-homo-21acetoxy-11,β,17aα-dihydroxy-pregna-1,4-dien-3,20-dione.

12. A compound according to claim 10 which is D-homo-21-acetoxy-11β,17α-dihydroxy-9α-fluoro-pregna-1,4-dien-3,20-dione.

13. A compound according to claim 10 which is D-homoprednisolone.

14. A compound according to claim 10 which is D-homo-9α-fluoroprednisolone.

15. A compound according to claim 10 which is 6α-fluoro-D-homoprednisolone.

16. A compound according to claim 10 which is 6α,-9α-difluoro-D-homoprednisolone.

* * * * *